(12) United States Patent
Aechtner

(10) Patent No.: US 9,918,908 B2
(45) Date of Patent: Mar. 20, 2018

(54) TWO-COMPONENT ADHESIVE FOR BONDING ARTIFICIAL TEETH TO A DENTURE BASE

(71) Applicant: Vita Zahnfabrik H. Rauter GmbH & Co. KG, Bad Sackingen (DE)

(72) Inventor: Stefan Aechtner, Bad Sackingen (DE)

(73) Assignee: Vita Zahnfabrik H. Rauter GmbH & Co. KG, Bad Säckingen (DE)

( * ) Notice: Subject to any disclaimer, the term of this patent is extended or adjusted under 35 U.S.C. 154(b) by 17 days.

(21) Appl. No.: 14/773,113

(22) PCT Filed: Mar. 10, 2014

(86) PCT No.: PCT/EP2014/054553
§ 371 (c)(1),
(2) Date: Sep. 4, 2015

(87) PCT Pub. No.: WO2014/139932
PCT Pub. Date: Sep. 18, 2014

(65) Prior Publication Data
US 2016/0015604 A1   Jan. 21, 2016

(30) Foreign Application Priority Data

Mar. 11, 2013 (EP) .................................... 13158639
Mar. 21, 2013 (EP) .................................... 13160316
Sep. 19, 2013 (EP) .................................... 13185167

(51) Int. Cl.
| | | |
|---|---|---|
| *C08K 5/00* | (2006.01) | |
| *C08L 33/00* | (2006.01) | |
| *C09J 133/00* | (2006.01) | |
| *C09J 4/06* | (2006.01) | |
| *A61K 6/083* | (2006.01) | |
| *C08F 220/14* | (2006.01) | |
| *A61K 6/00* | (2006.01) | |
| *C09J 133/12* | (2006.01) | |
| *A61C 13/10* | (2006.01) | |
| *C08F 222/10* | (2006.01) | |

(52) U.S. Cl.
CPC ............. *A61K 6/083* (2013.01); *A61C 13/10* (2013.01); *A61K 6/0023* (2013.01); *C08F 220/14* (2013.01); *C09J 4/06* (2013.01); *C09J 133/12* (2013.01); *C08F 2222/1013* (2013.01)

(58) Field of Classification Search
CPC ...... A61C 13/10; A61K 6/0023; A61K 6/083; C08F 220/14; C08F 2222/1013; C09J 133/12; C09J 4/06
See application file for complete search history.

(56) References Cited

U.S. PATENT DOCUMENTS

| | | | | |
|---|---|---|---|---|
| 4,182,035 | A | * | 1/1980 | Yamauchi ........... A61L 24/0073 260/998.11 |
| 4,548,992 | A | * | 10/1985 | Doi ............................ C09J 4/06 523/526 |
| 4,596,857 | A | * | 6/1986 | Doi ............................ C09J 4/06 524/417 |
| 4,792,577 | A | | 12/1988 | Chen et al. |
| 6,734,249 | B1 | * | 5/2004 | Bulluck ................. C09J 133/06 252/182.18 |
| 2004/0002037 | A1 | | 1/2004 | Orlowski et al. |

FOREIGN PATENT DOCUMENTS

| | | |
|---|---|---|
| CN | 101392153 A | 3/2009 |
| EP | 0452540 A1 | 10/1991 |
| JP | 55110174 A | 8/1980 |

OTHER PUBLICATIONS

Machine translation of EP0452540 downloaded Feb. 14, 2017.*

* cited by examiner

*Primary Examiner* — Irina S Zemel
*Assistant Examiner* — Jeffrey S Lenihan
(74) *Attorney, Agent, or Firm* — Christensen, Fonder, Dardi & Herbert PLLC; Curtis Herbert

(57) ABSTRACT

Dental adhesives and their uses, for instance an adhesive containing at least one first component A and at least one second component B, characterized in that said at least one first component A comprises a methyl methacrylate, a copolymer of methyl methacrylate dissolved in excess methyl methacrylate, at least one polyfunctional (meth)acrylate and a peroxide-based free-radical initiator, wherein said copolymer of methyl methacrylate is present in an amount of 30-50 parts by weight dissolved in a solution of 65-85 parts by weight of monomeric methyl methacrylate and 3-15 parts by weight of the polyfunctional (meth)acrylate, especially the triethylene glycol dimethacrylate (TEGDMA), mixed with a solution of 0.5 to 3 parts by weight of said peroxide-based free-radical initiator, especially dibenzoyl peroxide, in 70-90 parts by weight of monomeric methyl methacrylate, and said at least one second component B comprises methyl methacrylate and a tertiary amine.

14 Claims, 1 Drawing Sheet

TWO-COMPONENT ADHESIVE FOR BONDING ARTIFICIAL TEETH TO A DENTURE BASE

CROSS REFERENCE TO RELATED APPLICATIONS

This application is a national stage filing of PCT Application No. PCT/EP2014/054553 filed Mar. 10, 2014, which claims priority to European Applications EP 13158639.8 filed on Mar. 11, 2013, EP 13160316.9 filed Mar. 21, 2013, and EP 13185167.7 filed Sep. 19, 2013, all of which are incorporated herein by reference.

The present invention relates to a mixture containing at least one first component A and at least one second component B, to a dental prosthesis with a denture base and artificial teeth erected therein, and to uses of the mixture according to the invention.

INTRODUCTION TO THE INVENTION

Bonds between finished denture bases and teeth have previously been prepared by pretreating the adherend surfaces with primers. The primer partially dissolves the surface of the components to be bonded and enables improved penetration of the adhesive into the topmost substrate layers and thus achieves a higher strength of the adhesive bond. The pretreatment with primers is disadvantageous because it requires an additional operation. Such an additional operation is counterproductive, in particular, in modern mechanical production processes for partial or full prostheses. Therefore, it is desirable to provide an adhesive that can permanently bond artificial teeth to the denture base without pretreatment with primers.

U.S. Pat. No. 4,182,035 A discloses a composition for bonding hard tissues of the human body. It essentially contains a free-radically polymerizable polymer and a curing system containing a peroxide, an amine or salt thereof, and a salt of sulfinic acid.

EP 0 452 540 A1 discloses an adhesive for bonding molded parts of polycarbonate plastics.

A cold-curing two-component polymerization adhesive based on solutions of poly(methyl methacrylate) in alkyl methacrylate that additionally contain a di- and/or trimethacrylate can be used, in a temperature range of from −35° C. to +85° C., to prepare strong adhesive bonds between molded parts of polycarbonate that are resistant to water and fuels.

U.S. Pat. No. 6,734,249 B1 describes an acrylate adhesive that cures at room temperature and has an excellent dimensional stability. Such adhesives can be used, in particular, in applications for optical fiber connectors. Mixtures consisting of two parts are disclosed, wherein the first part contains one or more monofunctional, difunctional or trifunctional acrylates or acrylate monomers, a peroxide or hydroperoxide as initiator, and antioxidants and other additives. The second part represents an activator, which may contain, for example, N,N-disubstituted aromatic amines, a difunctional methacrylate monomer, an antioxidant, and optionally additives, such as thickeners, thixotropic agents and the like.

JP 55110174 or CN 200810198970 describe adhesive mixtures.

US 2004/0002037 A1 describes a method of securing a dental post in a correspondingly prepared tooth, crown or bridge. For securing, there is used a self-curing two-component cement prepared on the basis of an acrylate resin, and whose components are not mixed before application. The cement may also contain an aromatic tertiary amine and other components, such as an organic peroxide. Other additives may optionally be present.

U.S. Pat. No. 4,792,577 discloses an orthodontic adhesive consisting of two components that become reactive and cure without mixing when two layers of the different components come into contact. The first component has a relatively low viscosity and contains an acrylic or methacrylic diester of ethoxylated bisphenol A, an acrylic or methacrylic diester of an alkanediol, and benzyl acrylate or methacrylate. The second component contains a filler and an acrylic or methacrylic diester of ethoxylated bisphenol A, an acrylic or methacrylic diester of an alkanediol, and benzyl methacrylate or acrylate, wherein said filler is present in amounts within a range of from 50 to 80% by weight, based on the second component. One of the mentioned components contains a peroxide-based catalyst, and the other component contains a tertiary amine as activator for the peroxide catalyst.

SUMMARY

It is the object of the present invention to provide a mixture that can permanently bond artificial teeth to a denture base that, like the artificial teeth, is made of poly(meth)acrylate or its copolymers, leading to a prosthesis that will not result in adhesive failure of the bond upon critical load.

The object of the invention is achieved by a mixture containing at least one first component A and at least one second component B, characterized in that said at least one first component A comprises a methyl methacrylate, a copolymer of methyl methacrylate dissolved in excess methyl methacrylate, optionally comprising, additionally dissolved therein, at least one polyfunctional (meth)acrylate, especially ethylene glycol dimethacrylate, butanediol dimethacrylate, hexanediol dimethacrylate, triethylene glycol dimethacrylate (TEGDMA), tetraethylene glycol dimethacrylate, diurethane dimethacrylate, bis(hydroxymethacryloyloxypropoxy)-phenylpropane (bis-GMA), polyethylene glycol dimethacrylate, trimethylolpropane trimethacrylate, ditrimethylolpropane tetraacrylate; and a peroxide-based free-radical initiator, wherein said copolymer of methyl methacrylate is present in an amount of 30-50 parts by weight dissolved in a solution of 65-85 parts by weight of monomeric methyl methacrylate and 3-15 parts by weight of the polyfunctional (meth)acrylate, especially the triethylene glycol dimethacrylate (TEGDMA), mixed with a solution of 0.5 to 3 parts by weight of said peroxide-based free-radical initiator, especially dibenzoyl peroxide, in 70-90 parts by weight of monomeric methyl methacrylate, and said at least one second component B comprises methyl methacrylate and a tertiary amine.

DETAILED DESCRIPTION

Figure 1:
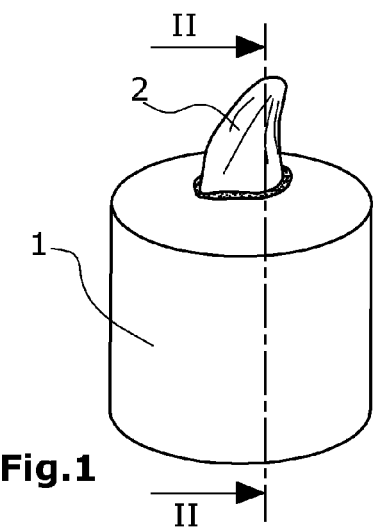
FIG. 1 shows a test specimen with a prosthetic tooth.

In another embodiment of the invention, said at least one first component A of the mixture according to the invention may comprise one or more polyfunctional (meth)acrylates, for example, ethylene glycol dimethacrylate, butanediol dimethacrylate, hexanediol dimethacrylate, triethylene glycol dimethacrylate (TEGDMA), tetraethylene glycol dimethacrylate, diurethane dimethacrylate, bis(hydroxymethacryloyloxypropoxy)phenylpropane (bis-GMA), polyethylene glycol dimethacrylate, trimethylolpropane trimethacrylate, ditrimethylolpropane tetraacrylate, etc.

According to the invention, the copolymer of methyl methacrylate is dissolved in an excess of methyl methacrylate in said at least one component A of the mixture according to the invention. In another embodiment of the invention, at least one of the mentioned polyfunctional (meth)acrylates, for example, ethylene glycol dimethacrylate, butanediol dimethacrylate, hexanediol dimethacrylate, triethylene glycol dimethacrylate (TEGDMA), tetraethylene glycol dimethacrylate, diurethane dimethacrylate, bis(hydroxymethacryloyloxypropoxy)phenylpropane (bis-GMA), polyethylene glycol dimethacrylate, trimethylolpropane trimethacrylate, ditrimethylolpropane tetraacrylate, etc., may be present dissolved in component A.

In another embodiment of the present invention, said at least one component A may be obtainable by dissolving the copolymer of methyl methacrylate in monomeric methyl methacrylate in the presence of at least one of the mentioned polyfunctional (meth)acrylates, for example, ethylene glycol dimethacrylate, butanediol dimethacrylate, hexanediol dimethacrylate, triethylene glycol dimethacrylate (TEGDMA), tetraethylene glycol dimethacrylate, diurethane dimethacrylate, bis(hydroxymethacryloyloxypropoxy)phenylpropane (bis-GMA), polyethylene glycol dimethacrylate, trimethylolpropane trimethacrylate, ditrimethylolpropane tetraacrylate, etc., and mixing with a solution of dibenzoyl peroxide in monomeric methyl methacrylate.

Typically, said tertiary amine present in the mixture according to the invention in said at least one component B is N,N-dimethyl-p-toluidine. In particular, said tertiary amine may be dissolved in amounts of 1-5 parts by weight in the form of N,N-dimethyl-p-toluidine in 65-85 parts by weight of monomeric methyl methacrylate.

The present invention also relates to a dental prosthesis with a denture base and artificial teeth erected therein, characterized in that said artificial teeth are permanently bonded to the denture base by means of the mixture according to the invention.

The present invention also relates to the use of the mixture according to the invention as a two-component adhesive, especially for preparing the dental prosthesis according to the invention. Typically, according to the invention, the mixture according to the invention may be used for bonding artificial teeth, especially made of PMMA and/or its copolymers, to a denture base, especially made of PMMA and/or its copolymers.

The present invention also relates to the use of the mixture according to the invention as a clear coat for sealing dental restorations, or of mixtures according to the invention colored by means of corresponding pigments for painting dental restorations.

The present invention also relates to a process for preparing the dental prosthesis according to the invention, characterized in that the artificial teeth are permanently bonded to the denture base by applying the mixture according to the invention to the areas of the artificial teeth coming into contact with the denture base, and/or applying the mixture according to the invention to the surfaces of the areas in the denture base in which the artificial teeth are arranged, and by curing the mixture.

Figure 3:
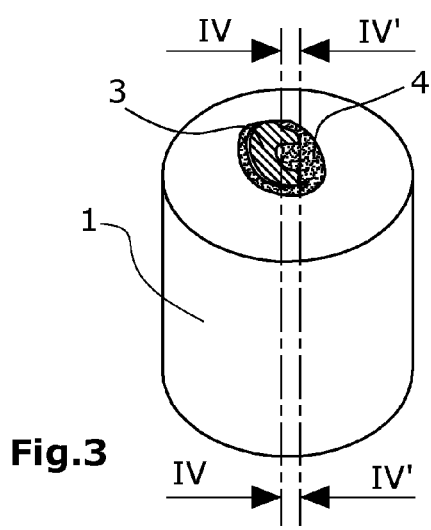
FIG. 3 shows a test specimen after a fracture test with a prosthetic tooth bonded with the adhesive according to the invention.
Figure 5:
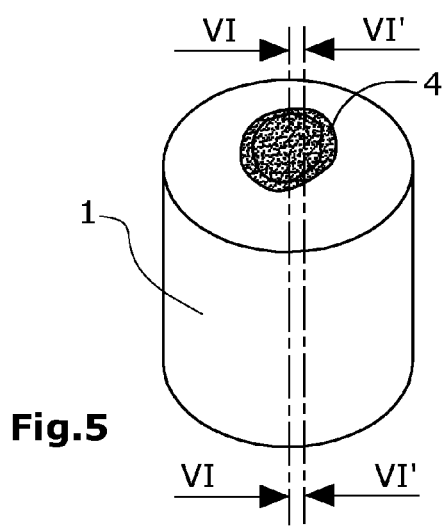
FIG. 5 shows a test specimen after a fracture test with a prosthetic tooth bonded with a conventional adhesive.
Figure 6:
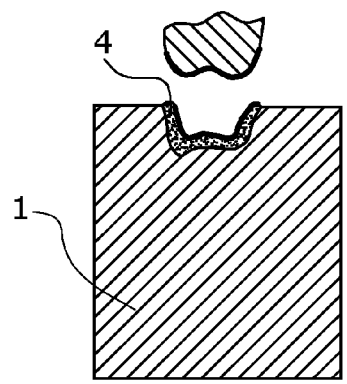
FIG. 6 shows a double section along the lines VI-VI and VI'-VI' through the test specimen of FIG. 5.

The prostheses obtained with the mixture according to the invention were subjected to fracture tests according to the standard DIN 13998. Experience has shown that adhesive failure of the adhesive is to be expected without previous pretreatment of the adherend sites with a primer. This was also confirmed experimentally for prosthetic teeth bonded with conventional adhesives (FIGS. 5 and 6). Surprisingly, the prostheses prepared with the mixture according to the invention exclusively showed cohesive fracture surfaces in the teeth and/or denture base (FIG. 3, 4).

The invention is further described hereinafter by means of the Examples.

Example 1

50 g of the copolymer of methyl methacrylate (Degacryl® MW 332, Evonik, Germany) is dissolved in a mixture of 100 g of methyl methacrylate and 10 g of triethylene glycol dimethacrylate (TEGDMA) supplied by Lehmann & Voss & Co., Germany (Luvomaxx® TEDMA). Thereafter, 2 g of dibenzoyl peroxide is dissolved in 80 g of methyl methacrylate, and to this solution is added 120 g of the first solution to obtain component A.

Component B is prepared as follows: 3 g of N,N-dimethyl-p-toluidine is dissolved in 75 g of methyl methacrylate.

Example 2

Component A as prepared in Example 1 was mixed with the mentioned component B at a ratio of 2:1 at room temperature. The mixture was applied either to the areas of the denture base coming into contact with the basal surface of the teeth, and/or to the basal surface of the artificial teeth, for example, with a paintbrush. The thus prepared prosthetic teeth were placed into the respective alveoli of the base. The thus prepared prosthesis was stored over night in an annealing furnace at 37° C. for the adhesive to cure.

Figure 2:
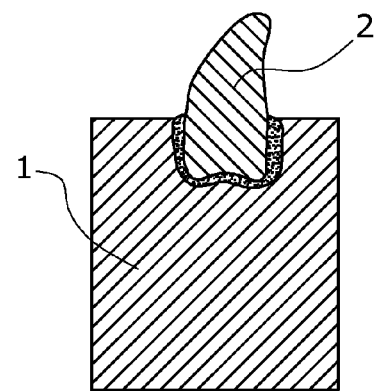
FIG. 2 shows a section along the line II-II of FIG. 1.
Figure 4:
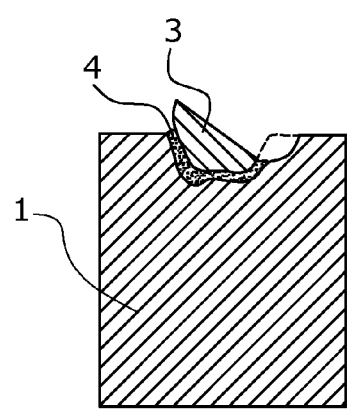
FIG. 4 shows a double section along the lines IV-IV and IV'-IV' through the test specimen of FIG. 3, taking into account the situation where even parts of the test specimen may be torn off during excavation.

With test specimens prepared in the same way (FIGS. 1 and 2), fracture tests according to the standard DIN 13998 were performed. The prostheses exclusively showed cohesive fracture areas in the teeth and/or base (FIGS. 3 and 4).

LIST OF REFERENCE SYMBOLS

1. Test specimens for fracture tests according to DIN 13998
2. Prosthetic tooth bonded into the test specimen
3. Remnant of the prosthetic tooth after cohesive failure
4. Adhesive residues

The invention claimed is:
1. A dental adhesive system mixture comprising:
at least one first component A and at least one second component B, wherein said at least one first component A comprises a methyl methacrylate, a copolymer of methyl methacrylate dissolved in excess methyl methacrylate, and a peroxide-based free-radical initiator, wherein said copolymer of methyl methacrylate is present in an amount of 30-50 parts by weight dissolved in a solution of 65-85 parts by weight of monomeric methyl methacrylate and 3-15 parts by weight of the polyfunctional (meth) acrylate, mixed with a solution of 0.5to 3 parts by weight of said peroxide-based free-radical initiator in 70-90 parts by weight of monomeric methyl methacrylate, and said at least one second component B comprises methyl methacrylate and a tertiary amine.

2. The adhesive system according to claim 1, wherein said at least one component A is obtainable by dissolving the copolymer of methyl methacrylate in monomeric methyl methacrylate in the presence of at least one polyfunctional (meth) acrylate, and mixing with a solution of dibenzoyl peroxide in monomeric methyl methacrylate.

3. The adhesive system of claim 1 wherein said tertiary amine in said at least one component B is N, N-dimethyl-p-toluidine.

4. The adhesive system of claim 3 wherein 1-5 parts by weight of N, N-dimethyl-p-toluidine is dissolved in 65-85 parts by weight of monomeric methyl methacrylate.

5. The adhesive system of claim 2 wherein the at least one polyfunctional (meth) acrylate comprises triethylene glycol dimethacrylate.

6. The adhesive system of claim 1 further comprising pigments for coloring in the mixture.

7. A dental prosthesis with a denture base and artificial teeth erected therein, comprising artificial teeth permanently bonded to the denture base with the adhesive system of claim 1.

8. The adhesive system of claim 1, wherein the adhesive system is a two component adhesive.

9. A process for preparing a dental prosthesis with a denture base and artificial teeth erected therein comprising:

applying the adhesive system of claim 1 to an area of the artificial teeth coming into contact with the denture base, and/or applying the adhesive system to the surfaces of the area in the denture base in which the artificial teeth are arranged, and after inserting the artificial teeth into the denture base and after curing the adhesive system, a permanent bond of the artificial teeth with the denture base is formed.

10. The adhesive system of claim 1 further comprising, additionally dissolved in component A, a polyfunctional (meth)acrylate, ethylene glycol dimethacrylate, butanediol dimethacrylate, hexanediol dimethacrylate, triethylene glycol dimethacrylate (TEGDMA), tetraethylene glycol dimethacrylate, diurethane dimethacrylate, bis(hydroxymethacryloyloxypropoxy)phenylpropane (bis-GMA), polyethylene glycol dimethacrylate, trimethylolpropane trimethacrylate, ditrimethylolpropane tetraacrylate , or triethylene glycol dimethacrylate (TEGDMA).

11. The adhesive system of claim 1 wherein said peroxide-based free-radical initiator comprises dibenzoyl peroxide.

12. A method of treating a patient comprising bonding artificial teeth to a denture base with the adhesive system of claim 1.

13. The method of claim 12 wherein the artificial base and/or the artificial teeth comprise polymethylmethacrylate and/or copolymers of methyl methacrylate.

14. A method of treating a dental restoration comprising using the adhesive system of claim 1 as a clear coat for sealing dental restorations or as a lacquer for painting dental restorations.

* * * * *